United States Patent
Fabian

(10) Patent No.: US 9,609,877 B2
(45) Date of Patent: Apr. 4, 2017

(54) COMPOSITION FOR EXTERMINATION OF BEDBUGS AND METHODS THEREOF

(71) Applicant: Cynthia Fabian, Somerset, NJ (US)

(72) Inventor: Cynthia Fabian, Somerset, NJ (US)

(73) Assignee: Cynthia Fabin, Venice, FL (US)

( * ) Notice: Subject to any disclaimer, the term of this patent is extended or adjusted under 35 U.S.C. 154(b) by 399 days.

(21) Appl. No.: 14/310,200

(22) Filed: Jun. 20, 2014

(65) Prior Publication Data

US 2015/0366218 A1    Dec. 24, 2015

(51) Int. Cl.
*A01N 59/00* (2006.01)
*A01N 65/28* (2009.01)
*A01N 65/26* (2009.01)

(52) U.S. Cl.
CPC ............. *A01N 65/28* (2013.01); *A01N 65/26* (2013.01)

(58) Field of Classification Search
CPC ......... A01N 65/28; A01N 65/26; A01N 59/00
See application file for complete search history.

(56) References Cited

U.S. PATENT DOCUMENTS

| | | |
|---|---|---|
| 2010/0205767 A1 | 8/2010 | Lewis |
| 2011/0064607 A1 | 3/2011 | Hedman |
| 2011/0229589 A1 | 9/2011 | Elraz |
| 2013/0026400 A1 | 1/2013 | Allen, Jr. |
| 2013/0089578 A1 | 4/2013 | Sumulong et al. |
| 2014/0352630 A1* | 12/2014 | Messina ................ A01N 49/00 119/712 |

OTHER PUBLICATIONS

Xiang, Yubin et al., Mocro-nanopores Fabricated by High-Energy Electron Beam Irradation: Suitable Structure for Controlling Pesticide Loss, 2013, Journal of Agricultural and Food Chemistry, vol. 61, pp. 5215-5219.*

* cited by examiner

*Primary Examiner* — Nannette Holloman
(74) *Attorney, Agent, or Firm* — Leason Ellis LLP.

(57) ABSTRACT

Disclosed herein is a composition for exterminating insects and prevent insect infestations. In one or more embodiments, the composition comprises Neem Oil, Clove Oil, and Diatomaceous Earth. Also disclosed is method for making the disclosed composition. Also disclosed are methods using and/or applying the composition to prevent and/or exterminate insect infestations.

20 Claims, No Drawings

US 9,609,877 B2

COMPOSITION FOR EXTERMINATION OF BEDBUGS AND METHODS THEREOF

1. INTRODUCTION

Disclosed herein are compositions and methods for exterminating insects. In certain embodiments, the composition is used for preventing and/or treating infestations of bedbugs. In certain embodiments, the composition is used for killing insects. In other embodiments, the composition is used for repelling insects and/or preventing insects from entering a particular area. Also disclosed are methods for making the compositions and methods for applying and/or using the composition. Provided herein are devices comprising the composition which are used to apply the composition.

2. BACKGROUND

Bedbugs have reemerged as a nuisance throughout the world in recent years. Bedbugs were thought to have been eradicated throughout most of the world several decades ago by the widespread use of powerful insecticides such as dichlorodiphenyltrichloroethane (DDT); however, because of many of the harmful effects of these powerful insecticides, their use has been banned in countries such as the United States. DDT and similar insecticides have since been replaced by less potent insecticides such as pyrethroids. As a result, bedbugs have developed resistance against these weaker insecticides, and thus have again become a persistent pest in human dwellings, and in particular homes, hotels and motels.

Bedbugs are parasitic insects that feed primarily on human blood as well as the blood of domesticated animals. They are typically active at night, and their bites can leave visible, itchy welts on the skin of their victims if allergic. Bedbugs often enter dwellings in luggage, clothing, or other items, and typically live in places near the sleeping areas of humans, such as walls, mattresses, bed frames, and box springs. Because bedbugs are capable of reproducing multiple times a year, infestations can be very difficult to exterminate. This is particularly true for multi-person dwellings such as apartment buildings, hotels, and motels, where separate dwellings have adjoining and/or adjacent physical separation, such as a wall, such that bedbugs have access to multiple human victims. In addition, the growing resistance of bedbugs to current insecticides, the increase in the amount and types of international travel has further exacerbated the spread of bedbugs, particularly in major metropolitan areas. Further, current attempts to curb bedbug infestations have largely been ineffective. For instance, some chemical insecticides have been applied to affected areas, such as a mattress; however that can expose those using the mattress or infected areas to the odors and other effects of chemical pesticides. In contrast, insect exterminator services often use gel-based pesticides that have low toxicity; however, these types of pesticides—while effective against most other insects—are not capable of eliminating bedbug infestations.

Thus, based on the growing resistance of bedbugs to current pesticides and the spread of bedbugs through domestic and international travel, there is a need for a safe and effective way to exterminate bedbugs.

3. SUMMARY

Provided herein is a composition for the extermination of bedbugs. In one or more embodiments, the composition consists of Neem Oil, Clove Oil, and Diatomaceous Earth. In one embodiment, the composition further consists of an acid, such as vinegar. In at least one embodiment, the composition is sterilized prior to administration.

Provided herein is a method for making the composition comprising mixing Neem Oil, Clove Oil and Diatomaceous Earth and irradiating the mixture with gamma rays. Provided herein is a method for exterminating, repelling, preventing infestation of bedbugs comprising administering an effective amount of the composition in particular locations near the bed area. In one or more embodiments, the composition is administered into a physical separation. In one embodiment, the physical separation is a wall. In at least one embodiment, the composition is administered into a mattress. In one or more embodiments, the composition is administered around a bed frame. Also provided herein is a kit for administering the disclosed composition.

4. DEFINITIONS

When referring to the compounds and/or compositions provided herein, the following terms have the following meanings unless indicated otherwise.

"Effective amount" includes an amount of a compound or composition that, when applied or administered to a particular surface and/or area is sufficient to treat an infestation. An "effective amount" can vary depending on, inter alia, the compound or composition applied, the severity of the infestation, and the location of the infestation.

"Treating" or "treatment" of the infestation can refer to administering a compound or composition to combat an existing infestation or to prevent a future infestation.

The term "sterilization" can be defined as any process that effectively kills or eliminates transmissible agents (such as fungi, bacteria, viruses and prions) from a surface, equipment, foods, medications, or biological culture medium.

"Exterminating" or "exterminate" means to eliminate an existing infestation of insects and/or to kill existing insects.

5. DETAILED DESCRIPTION

Insect infestations have been on the rise throughout the world, particularly in multi-family dwellings, such as hotels, motels, apartment buildings, and condominiums. Currently available chemical pesticides are effective against pests such as cockroaches, ants, bedbugs, silverfish, ladybugs. However, these insects have increasingly developed resistance against these pesticides. In light of the lack of success and the potentially harmful side effects of using such chemical pesticides, natural compounds have been explored as a way of exterminating insects. The present disclosure is based on the surprising discovery that the combination of Neem Oil, Clove Oil and Diatomaceous Earth has a synergistic effect of repelling, preventing and terminating insect infestation. The surprising effectiveness of this composition is demonstrated in section 6. The disclosed composition is safe and effective extermination of insects. In certain embodiments, the composition is effective against cockroaches, ants, bedbugs, silverfish, ticks, mites, ladybugs. In a particular embodiment, the insect is bedbugs.

5.1 COMPOSITION

Disclosed herein is a composition for the extermination of insects. Provided herein is a composition comprising Neem Oil, Clove Oil, and Diatomaceous Earth. In one embodiment, the composition is used to treat and/or prevent bedbug infestations. Also disclosed herein are methods for making the composition. Disclosed herein are methods for using and/or applying the composition.

Neem Oil is a derived from the fruits and seeds of a neem tree (*Azadirachta indica*), a tropical evergreen tree. Neem Oil is considered a Generally Recognized as Safe (GRAS) substance and is typically regarded as nontoxic to the environment and mammals, and heat and/or ultraviolet rays promotes its degradation. Neem Oil and its derivatives can contribute to controlling pests including insects (e.g. bedbugs), ticks, and mites by affecting the physiology and behavior of the pests. Neem Oil alone does not typically kill pests immediately but it can affects pests' growth as well as deter them. Contrastingly, Neem Oil and products derived from Neem are typically not toxic to higher animals or "non-pest" insects. Neem Oil can comprise of several compounds including Azadirachtin, Meliantriol, Nimbin, and Salannin. Neem Oil used in accordance with the present application can contain between 10-90% of Azadirachtin by weight, 10-90% of Meliantriol by weight, 10-90% of Nimbin by weight, and 10-90% of Salannin by weight.

Clove Oil is derived from the clove plant, *Syzygium aromaticum*. Clove Oil is also considered a GRAS substance, and can be used as an additive to human food. Clove Oils can be extracted from various parts of the clove plant including roots, stems, buds, and leaves. Clove Oils can comprise a mixture of several different compounds, including eugenol, isoeugenol, and methyleugenol. Clove Oil used in accordance with the present application can contain between 10-90% of eugenol by weight, 10-90% of isoeugenol by weight, and 10-90% of methyleugenol by weight.

Diatomaceous Earth consists of fossilized remains of diatoms, a type of hard-shelled algae. Diatomaceous Earth, (also known as DE, diatomite, diahydro, kieselguhr, kieselgur and Celite) is a naturally occurring, soft, chalk-like sedimentary rock that is easily crumbled into a fine white to off-white powder. This powder has an abrasive feel, similar to pumice powder, and is very light, due to its high porosity. According to the EPA (Environmental Protection Agency, USA) RED (Registration Eligibility Documents) Facts, September 1991, Diatomaceous Earth (silicon dioxide), has low to moderate acute toxicity (Category III) and is not considered a carcinogen.

A typical chemical composition of Diatomaceous Earth is 86% silica, 5% sodium, 3% magnesium and 2% iron. In certain embodiments, the chemical composition of Diatomaceous Earth can range from 60-90% of silica, 1-10% of sodium, 1-10% of magnesium and 1-10% of iron. In other embodiments, Diatomaceous Earth is of food grade. Diatomaceous Earth is typically in the form of a dust made from granulated fossil shells. A thin dusting of the disclosed composition in places where it will not be disturbed can be helpful in killing bed bugs. The composition described herein is useful for augmenting treatment or as a preventative treatment against new infestations.

The composition in accordance with one or more embodiments of the present application consists of Neem Oil, Clove Oil, and Diatomaceous Earth. The percentage by weight of Neem Oil, Clove Oil, and Diatomaceous Earth in embodiments of the composition can vary. In accordance with one or more embodiments, the percentage by weight of Neem Oil can range between 0.1-0.5%, 0.5-1%, 1-2%, 2-4% and 4-10%; the percentage by weight of Clove Oil can range between 0.1-0.5%, 0.5-1%, 1-2%, 2-4% and 4-10%; and the percentage by weight of Diatomaceous Earth can range between 10-20%, 20-40%, 40-50%, 50-60%, 60-70%, 70-80-%, 80-90% and 90-95%. In one embodiment, the composition is 1-20% Neem Oil by weight, 1-20% Clove Oil by weight, and 60-98% Diatomaceous Earth by weight. In certain embodiments, the ratio of Neem Oil to Clove Oil to Diatomaceous Earth is 1:1:1. In certain embodiments, the composition can further comprises an acid. In one embodiment, the acid is vinegar. In other embodiments, the composition can further comprises water, gel and solvent.

The compounds disclosed herein can be formulated into compositions in accordance with one or more embodiments of the present application using methods available in the art and those disclosed herein. Such compounds can be used in certain embodiments to enhance delivery of the composition to a location. The composition has more than an additive effect which is not found in each of the component when administered alone or with two of the three components. The composition has a synergistic effect that is not found in each of the component when administered alone or with two of the three components. In certain embodiments, the disclosed composition is 5-10 times, 10-20 times, 20-40 times, 40-80 times, 80-100 times more effective than each component alone or with combinations of only two of the three components. This can be measured with ANOVA Software. A synergistic effect of a combination of the compound permits the use of small amounts of the disclosed composition and/or less frequent administration of said composition for extermination of pests. The ability to utilize small amounts of the composition and/or to administer said composition less frequently reduces the cost associated with the administration of said treatment to an infected area without reducing the efficacy of said composition in the prevention or treatment of the infestation. In addition, a synergistic effect can result in improved efficacy of the composition in the prevention or treatment of an infestation.

In certain embodiments, the compositions described herein can be used with or without a carrier. A "carrier," as described herein, refers to an inert material that can be organic or inorganic and of synthetic or natural origin, with which the active compound can be formulated or mixed to facilitate its application to a surface or other object to be treated, and/or its storage, transport, and/or handling. Generally, any of the materials typically employed as a carrier in formulating pesticides are suitable for use in accordance with one or more embodiments. The compositions provided herein can be used alone or in the form of mixtures with such solid and/or liquid dispersible carrier. Examples of suitable carriers include conventional inert pesticide diluents or extenders of the type useable in conventional pesticide compositions, e.g., conventional pesticide dispersible carrier vehicles such as solutions, emulsions, suspensions, emulsifiable concentrates, spray powders, pastes, soluble powders, dusting agents, granules, foams, pastes, tablets, aerosols, natural and synthetic materials impregnated with active compounds, microcapsules, fumigating cartridges, fumigating cans and fumigating coils, as well as cold mist and warm mist formulations.

More specifically, examples of conventional carriers suitable for use herein include but are not limited to: aerosol propellants, which are gaseous at normal temperatures and pressures, such as propane, butane, isobutene and carbon dioxide; inert dispersible liquid diluent carriers, including inert organic solvents, such as aromatic hydrocarbons (e.g., benzene, toluene, xylene, alkyl naphthalenes), halogenated aromatic hydrocarbons, cycloalkanes (e.g., cyclohexane), paraffins (e.g., petroleum or mineral oil fractions), chlorinated aliphatic hydrocarbons (e.g., methylene chloride, chloroethylenes), alcohols (e.g., methanol, ethanol, propanol, butanol, ethylene or propylene glycol) as well as ethers and esters thereof (e.g., glycol monomethyl ether), amines (e.g., ethanolamine), amides (e.g., dimethyl formamide), sulfoxides (e.g., dimethyl sulfoxide), acetonitrile, ketones (e.g., acetone, methyl ethyl ketone, methyl isobutyl ketone, cyclohexanone), and/or water; as well as inert dispersible finely divided solid carriers such as ground natural minerals (e.g., kaolins, clays, vermiculite, alumina, silica, chalk, i.e., calcium carbonate, talc, attapulgite, montmorillonite, kieselguhr), and ground synthetic minerals (e.g., highly dispersed silicic acid, and silicates, e.g., alkali silicates).

5.2 METHOD OF MAKING THE COMPOSITION

Disclosed herein are methods for making the disclosed composition. One or more embodiments of the present application consist of a method of making the disclosed composition using gamma rays. More specifically, in at least one embodiment, the Neem Oil, Clove Oil, and Diatomaceous Earth are irradiated in order to produce the disclosed composition. In one embodiment, the irradiation is gamma rays. Alternatively, the composition can be freeze dried. One skilled in the art uses gamma rays irradiation to combine substances of different types. Other different techniques that are known in the art to combine various substances can be used. In certain embodiment, the composition is sterilized so as to make the composition free of transmissible biological agents such as bacteria or virus. In certain embodiments, sterilization is achieved by exposure of the object to be sterilized to chemical or physical agent(s) for a specified time. Various agents that can be used to sterilize the composition include elevated temperature, ionizing radiation, chemical liquids, and gases. One skilled in the art can determine the most suitable choice of the method adopted for sterilization.

5.3 METHODS OF USING AND ADMINISTERING THE COMPOSITION

In one or more embodiments, the composition can be combined with a canning process with, for instance, an aerosol can similar to a can used for dry shampoo or mousse. For example: 1) dispersion dryers can be used for continuous slurry drying of high moisture materials; 2) paddle dryers can then be used for wet cake drying; and 3) fluid bed dryers and reactors can be used to meet low-moisture (PPM) final product requirements. This type of process can result in the combining of a powder (e.g., Diatomaceous Earth) and oils (e.g., Neem Oil and Clove Oil). A canning process in accordance with one or more embodiments could also be used to dispense the composition using a spray bottle. In one embodiment, the composition is placed in only one can, canister, or bottle, thereby not having to waste applicators and pre-wrapped cellophane. In one or more embodiments, the can or canister comprising the disclosed compositions is cylindrical in shape and/or can have a remote trigger such that the remote trigger actuates a valve, thereby dispensing the composition.

5.3.1 ADMINISTRATION OF THE COMPOSITION AS A POWDER

In one or more embodiments, the disclosed composition can also be administered in powder form in and around the infected area.

In terms of efficacy, the disclosed composition in powder form should not be used in conjunction with other pesticide treatments without consultation with a Pest Control Operator. The use of other common pesticide substances with the disclosed composition in powder form may limit the effectiveness of the disclosed composition.

In terms of safety, although fresh water and/or food grade Diatomaceous Earth is safe if used properly, a good respirator mask should be used when applying any dust or powder formulation, such as one in accordance with an embodiment of the present application, as well as using a disposable waterproof gloves when applying it. In addition, large quantities of powder in accordance with an embodiment should not be used as they are likely to be kicked up and inhaled. Additionally, powder formulations in accordance with the present application should not be administered on windowsills, couch cushions, or beds where a breeze might blow the dust around. Additionally, a powder formulation in accordance with the present application should not be placed in any areas that will be in direct contacted with human or pet.

The powder formulations of the present application can be used in areas where the pests are present and where the powder will subsequently be left undisturbed. These areas include cracks or crevices in the floor or wall, and voids in the wall. Additionally, the area in which the powder is administered should be ventilated after administration, but before safety gear has been removed. Finally, if the room in which the powder is administered is vacuumed often (as can be necessary during treatments), a thin coating of the powder can be re-applied after vacuuming. Vacuuming should be as infrequently as possible however, as the powder can wear out a vacuum more quickly than normal dirt and dust.

5.3.2 ADMINISTRATION OF THE COMPOSITION INTO A WALL

In certain embodiments, the powder formulation of the disclosed composition may be applied into the wall by first drilling an opening and then deposit the composition therein. In one or more embodiments, the opening or hole can be approximately ¾ inches thick; however other size holes may be employed since the powder will disperse once it is squeezed into wall. Once the hole or holes have been drilled into the wall, in accordance with at least one embodiment, a squeeze bottle can be used to apply the composition into the hole(s).

In one or more embodiments, white vinegar can then be applied via a spray bottle to the areas in which the powder was applied. In other embodiments, the vinegar can be dried into the powder composition, however, it is most effective if used fresh as a follow up to the application of the powder composition to keep pests away. For example, following the drilling and the application of a powder formulation of the disclosed composition into the wall, vinegar may be applied at the location(s) where the powder was applied, as well as the baseboards of the wall. After a few days of applying vinegar, there is no need for further application or follow up with vinegar.

Different types of bottles may be used for the application of the composition and/or application of the acid (e.g., vinegar). For example, a squeeze bottle can be used for application of the composition and/or acid. In other embodiments, a small applicator tube can be used for application of the composition and/or acid. Further, a tube or applicator can be pre-loaded for single use in instances in which the user prefers to have each use pre-measured. Alternatively, the applicator can be preloaded with multiple uses. This type of tube is utilized by cutting the tip and squeezing. Additionally, in one or more embodiments, a spray bottle can be used for the application of the disclosed composition and/or acid.

In other embodiments, the composition(s) provided herein can be administered by other delivery devices that are well known to those of ordinary skill in the art.

5.3.3 ADMINISTRATION OF THE COMPOSITION BY THE BED

Also provided are embodiments in which the disclosed composition can be applied in areas around the bed. In particular, the disclosed composition can be administered to areas around and under the bed so long as those areas will not be disturbed. In one or more embodiments, the disclosed composition can be applied directly in the mattress. The composition can be applied in between the mattress and the box spring, supporting frame or platform support.

5.4 KIT COMPRISING THE COMPOSITION

Also provided are kits for use in the extermination of bedbugs. The kits can include the disclosed composition(s) described herein, additional agent(s), and instructions providing information to a user regarding usage for treating the infestation. Instructions can be provided in printed form as well as in the form of an electronic medium such as a floppy disc, CD, or DVD, and in the form of a website address where such instructions may be obtained. A unit dose of a compound or composition described herein, or a second agent or composition, can include the amount of the composition to be used such that when administered, an effective level of the compound or composition can be maintained in the area of application for a specified amount of time. (Total grams of composition 21.44 grams of DE, 2 grams each of Clove Oil and Neem Oil a total of 25.44 grams.)

In certain embodiments, the disclosed composition included in the kit can be a sterile aqueous composition or dry powder composition. In some embodiments, suitable packaging is provided. As used herein, "packaging" can include a solid matrix or material customarily used in a system and capable of holding within fixed limits a compound provided herein and/or a second agent suitable for administration. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

Breathing (respirator) masks can also be included in the kit. It is recommended that that the users cover their mouth and nose with the masks while applying any powder substance. The air settles approximately 10 minutes after application (e.g., when applied after drilling into the wall) and there is no need to wear a mask thereafter. Further, disposable waterproof gloves can be included in the kit for use during the application of the composition. Additionally, wall plugs can also be included in the kit in various sizes. In certain embodiments, the composition is administered in the form of a wall plug. In certain embodiments, the composition is administered through a deposit device and a wall plug is used after the deposit device is inserted into the wall. Further, in one or more embodiments, the kit can include a type of wall filler, spackle in airtight packaging, and spackle utensils including spackle knives.

6. EXAMPLES

The following examples illustrate the synthesis and use of representative compositions provided herein. These examples are not intended, nor are they to be construed, as limiting the scope of the claimed subject matter. It will be clear that the scope of subject matter may be practiced otherwise than as particularly described herein. Numerous modifications and variations of the subject matter are possible in view of the teachings herein and, therefore, are within the scope the claimed subject matter.

6.1 MAKING THE COMPOSITION VIA GAMMA RAYS

1st—Powder: Diatomaceous Earth (21.44 grams or 1 tablespoon)
2nd—Oil: Neem Oil (2 grams)
3rd—Oil: Clove Oil (2 grams)
4th—Acid or white vinegar—(This is optional component and applied using a spray bottle and spray liberally. (0.5 gram)

Gamma Rays are used to irradiate and combine all of the ingredients: Diatomaceous Earth, Clove Oil and Neem Oil. Gamma Ray procedure can be done in a factory or using various methods as known in the art.

6.2 APPLYING THE COMPOSITION—DEPOSIT THROUGH DRILLING A WALL OR A SEPARATION

In this example, an embodiment of the disclosed composition was used to combat an infestation of bedbugs, which was located in a wall adjacent to a bed. In this example, the composition comprises 21.44 grams or 1 tablespoons of Diatomaceous Earth, 2 grams of Neem Oil, and 2 grams of Clove Oil. The ingredients were mixed together in a mixing bowl to produce the composition, and the resulting composition was wrapped in cheesecloth as a paste.

A hole was then drilled into the wall containing the bedbugs. The hole was approximately 0.75 inches deep. Using an applicator, the composition was then pushed into the wall through the hole. The powder dispersed once it was squeezed into wall through the cheesecloth. A round plug matching the circumference of the hole was then used to plug the hole.

This procedure was repeated 4 additional times, such that a total of 5 holes in the wall were created and the composition was applied in each hole. Vinegar was then applied as a follow-up on the baseboards of the wall and near the holes where the composition was applied into the wall. In less than a week, the infestation was eliminated, and no new living bedbugs were seen after one week. 100% of bedbugs were exterminated. Hundreds of dead bedbugs were cleaned up after one week.

In the control, when each of the components of the composition was used individually for the same procedure, there were no effects to the bedbugs after more than two months. In fact, the bedbugs continue to multiply when each component was used. Even when two out of the three components were used for the same procedure, there were not much effects to the bedbugs after more than two months and the bedbugs continue to multiply when two out of the three components were used.

6.3. THE COMPOSITION PROVIDES SYNERGISTIC EFFECT FOR THE EXTERMINATION OF BEDBUGS

This example shows the effectiveness of an embodiment of the disclosed composition compared with the individual components of the disclosed composition and other combinations of those components.

Group 1. 40 bedbugs were analyzed using ANOVA software was exposed to 21.44 g of Diatomaceous Earth in powder form. The bedbugs were then observed once a day to determine the mortality rates. The results showed that Diatomaceous Earth did not begin to kill the bedbugs until 20 days after exposure. At 0.05 confidence level 92% of samples showed a significant mortality rate.

Group 2. 20 experiments were done with 40 bedbugs exposed to 10 g in each sample's and results were analytical using ANOVA Software. At 0.05 confidence level 89% of samples show significant mortality initiated after 20 days of exposure. The bedbugs were exposed to Neem Oil. The bedbugs were then observed once a day to determine the mortality rates. However, Neem Oil did not begin to kill the bedbugs until 20 days after exposure.

Group 3. 20 experiments were done with 40 bedbugs exposed to 10 g in each sample's and results were analytical using ANOVA Software. At 0.05 confidence level 94% of samples show significant mortality initiated after 20 days of exposure. The bedbugs were exposed to Clove Oil. The bedbugs were then observed once a day to determine the mortality rates. The results showed that Clove Oil did not begin to kill the bedbugs until 20 days after exposure.

Group 4A. 20 experiments were done with 40 bedbugs exposed to 21.44 g of DE and 2 g of Clove Oil. The Results were analytical using ANOVA Software. At 0.05 confidence level 93% of samples show significant mortality initiated after 20 days of exposure.

Group 4B. 20 experiments were done with 40 bedbugs exposed to a combination of 2 g of Neem Oil and 21.44 g of Diatomaceous Earth. The bedbugs were then observed once a day to determine the mortality rates. The results showed that the combination of Diatomaceous Earth and Neem Oil began to kill the bedbugs after 20 days of exposure.

Group 5. 40 bedbugs were exposed to a combination of 10 g of Neem Oil and 10 g of Clove Oil. The bedbugs were then observed once a day to determine the mortality rates. The Results were analytical using ANOVA Software. At 0.05 confidence level 92% of samples show significant mortality initiated after 20 days of exposure. The results showed that the combination of Neem Oil and Clove Oil began to kill the bedbugs after 20 days.

Group 6. 40 bedbugs were exposed to a combination of 2 g of Neem Oil, 2 g of Clove Oil, and 21.44 g of Diatomaceous Earth. The bedbugs were then observed once a day to determine the mortality rates. The results were analytical using ANOVA Software. At 0.05 confidence level 99% of samples show significant mortality initiated after 20 days of exposure. The results showed that the combination of Neem Oil, Clove Oil, and Diatomaceous Earth killed 99% of the bedbugs within 7 days.

Group 7. 40 bedbugs were exposed to 10 g of water, sprayed into a Petrie dish (the control group). The bedbugs were then observed once a day to determine the mortality rates. The results showed that exposure to water began to kill the bedbugs after 30 days.

The results of this example show that the combination of Neem Oil, Clove Oil, and Diatomaceous Earth—the components for the disclosed composition—had not just an additive effect but a synergistic effect for the extermination of bedbugs.

The invention is not to be limited in scope by the specific embodiments described herein. Various modifications in addition to those described herein will become apparent to those skilled in the art from the foregoing description and accompanying figures. Such modifications are intended to fall within the scope of the appended claims.

The invention claimed is:

1. A composition for the extermination of bedbugs comprising a combination of:
    a) Neem Oil,
    b) Clove Oil, and
    c) Diatomaceous Earth, wherein each ingredient is irradiated; wherein the combination has a synergistic effect.

2. The composition of claim 1 further comprising an acid.

3. The composition of claim 2, where the acid comprises a vinegar.

4. The composition of claim 1 further comprising at least one compound selected from the group consisting of carriers and excipients.

5. The composition according to claim 4, wherein the carrier is a mineral.

6. The composition according to claim 4, comprising a carrier.

7. The composition according to claim 4, wherein the carrier is a vegetable-based organic product.

8. The composition according to claim 4, wherein the carrier is another oil-based product.

9. The composition according to claim 1, wherein the composition is sterilized.

10. The composition according to claim 1, wherein the composition is 1-20% Neem Oil by weight, 1-20% Clove Oil by weight, and 60-98% Diatomaceous Earth by weight.

11. A method for making a composition comprising: (i) mixing Neem Oil, Clove Oil, and Diatomaceous Earth to form a mixture; (ii) irradiating the mixture.

12. A method of exterminating bedbugs comprising applying the composition of claim 1.

13. The method of claim 12 wherein the composition is applied under a mattress.

14. The method of claim 12 wherein the composition is applied in a physical separation, the method comprises applying the composition to a hole in the physical separation.

15. The method of claim 14 further comprising the step of applying vinegar to the physical separation.

16. The method of claim 14 wherein the physical separation is a wall.

17. A kit comprising the composition of claim 1.

18. The kit of claim 17 wherein the composition is in a canister and instructions.

19. The kit of claim 18 further comprising a remote trigger that actuates a valve thereby causing the composition to be dispensed.

20. The kit of claim 18 wherein the canister further comprises a nozzle with a spray tip.

* * * * *